United States Patent [19]

Abatjoglou et al.

[11] Patent Number: 4,518,805

[45] Date of Patent: May 21, 1985

[54] PROCESS FOR REMOVING HYDROPEROXIDES AND ALDEHYDES FROM ALLYL-ALKYL ETHER

[75] Inventors: Anthony G. Abatjoglou; David R. Bryant, both of Charleston, W. Va.

[73] Assignee: Union Carbide Corporation, Danbury, Conn.

[21] Appl. No.: 466,023

[22] Filed: Feb. 14, 1983

Related U.S. Application Data

[63] Continuation of Ser. No. 243,082, Mar. 12, 1981, abandoned.

[51] Int. Cl.³ ............................................. C07C 45/50
[52] U.S. Cl. ..................................... 568/444; 568/454; 568/693; 568/579
[58] Field of Search .............. 568/579, 693, 621, 580, 568/581, 701, 444, 454

[56] References Cited

U.S. PATENT DOCUMENTS

| | | |
|---|---|---|
| 1,935,658 | 11/1933 | Nitardy . |
| 1,971,930 | 8/1934 | Christiansen et al. . |
| 2,056,972 | 10/1936 | Lott . |
| 2,107,069 | 2/1938 | Evans ................................. 568/581 |
| 2,121,019 | 6/1938 | Christiansen et al. . |
| 2,957,023 | 10/1960 | Dimler et al. ................. 568/701 X |
| 3,003,002 | 10/1961 | Feinstein ............................ 260/616 |
| 3,065,258 | 11/1962 | Dimler et al. ................. 568/701 X |
| 3,168,569 | 2/1965 | Matell . |
| 3,221,030 | 11/1965 | Huffman ........................ 568/580 X |
| 3,629,288 | 12/1971 | Vit . |
| 4,107,099 | 8/1978 | Hedge ............................. 568/862 X |

FOREIGN PATENT DOCUMENTS

| | | |
|---|---|---|
| 876034 | 8/1961 | United Kingdom . |
| 981965 | 2/1965 | United Kingdom . |
| 1032633 | 6/1966 | United Kingdom . |

Primary Examiner—Bernard Helfin
Attorney, Agent, or Firm—Reynold J. Finnegan

[57] ABSTRACT

Described herein is a process for the conversion of hydroperoxides, present in allyl-alkyl ethers to products including $\alpha,\beta$-unsaturated aldehydes and for reducing such $\alpha,\beta$-unsaturated aldehydes to alcohols prior to the use of the ether as a feedstock in a hydroformylation reaction to produce the corresponding ether aldehyde. The process involves contacting the ether with a metal hydride, either in aqueous solution and/or by means of an ion exchange resin. Such treatment decomposes the hydroperoxides and then reduces their $\alpha,\beta$-unsaturated aldehyde decomposition products, thereby reducing the catalyst inhibition period present in the hydroformylation reaction which is observed when such $\alpha,\beta$-unsaturated aldehyde impurities are present.

4 Claims, No Drawings

PROCESS FOR REMOVING HYDROPEROXIDES AND ALDEHYDES FROM ALLYL-ALKYL ETHER

This application is a continuation of our prior U.S. application Ser. No. 243,082 filed Mar. 12, 1981, and now abandoned.

BACKGROUND OF THE INVENTION

This invention is directed to a process for the conversion of hydroperoxides present in allyl-alkyl ether to enhance the use of such ether as a feedstock in a rhodium catalyzed hydroformylation process to produce the corresponding ether aldehyde. Such hydroperoxides are decomposed by treating the ether with metal hydride to give products which include α,β-unsaturated aldehydes, which are then reduced to the corresponding alcohols.

Hydroperoxides, which may form in allyl-alkyl ether by adventitious air oxidation, decompose during hydroformylation to form α,β-unsaturated aldehydes such as acrolein, among other by-products. The effect of acrolein and closely related compounds as rhodium catalyst inhibitors is known in the prior art. U.S. Pat. No. 4,148,830 issued Apr. 10, 1979, indicates, at Column 4 lines 65 et. seq., that it is highly desirable to maintain "substituted acrolein II" (i.e., ethylpropylacrolein) at low concentrations "since it has been observed that a build-up of this product tends to curtail the life of the rhodium complex catalyst."

The effect of the presence of acrolein in allyl-alkyl ether used as a feedstock in a rhodium catalyzed hydroformylation reaction to produce the corresponding ether aldehyde is seen in Example 1 in Table I below. It is postulated that this catalyst induction period occurs because of the competition for the rhodium catalyst between the hydroformylation reaction and the reaction to reduce acrolein to propanol and/or propionaldehyde. Such a catalyst induction period is effectively eliminated by removing hydroperoxides and acrolein from the allyl-alkyl ether. See Examples 2-4, infra, and Table I below.

According to J. A. Riddick and W. B. Bunger, "Techniques of Chemistry" Vol. 2, p. 690 "Organic Solvents" Wiley-Interscience (1970), solutions of phenothiazine, iron (II) sulfate, tin (II) chloride, copper-zinc couple, sodium bisulfite, alkali metal hydroxides, cerium (III) hydroxide and lead (IV) oxide have all been found to destroy peroxides in ethers. However, none of the above reagents is known to be effective in removing or reducing acrolein as well.

Riddick and Bunger, supra at p. 691 also discloses that passing impure ether through an activated aluminum oxide column will reduce aldehyde content as well as remove peroxide. However, research has revealed that only a relatively small quantity of acrolein is adsorbed on the alumina and retained (See Example 2 and Table I below). Thus alumina cannot effectively be used for the purification of large quantities of allyl-alkyl ether without adding complicated and expensive processing steps to avoid eventual acrolein breakthrough with the allyl-alkyl ether effluent.

M. Ross Johnson and Bruce Rickborn "Sodium Borohydride Reduction of Conjugated Aldehydes and Ketones", J. Org. Chem. Vol. 35, p. 1041 (1970) show the use of aqueous alkali metal borohydrides as reducing agents for aldehydes, including the reduction of acrolein to allyl alcohol and propanol. Similarly, British Pat. No. 981,965 describes the use of alkali metal borohydride to reduce the residual aldehyde content in Oxo alcohol after hydroformylation. However, neither reference discloses the use of alkali metal borohydrides to reduce hydroperoxides and simultaneously to reduce the acrolein formed during the reduction of the hydroperoxides in allyl-alkyl ethers.

U.S. Pat. No. 3,003,002 discloses a means of removing peroxides from diethyl ether by contact with a strong base anion exchange resin in its hydroxyl form. However, this treatment will only remove peroxide and will not remove aldehydes, as such bases will not react with α,β-unsaturated aldehydes in such manner as to tie them up.

British Pat. No. 876,034 and U.S. Pat. No. 4,107,099 both disclose the manufacture of borohydride exchange resins. In addition, U.S. Pat. No. 4,107,099 contains several examples of the use of such resins. Example 12 discloses the reduction of crotonaldehyde, as an undesirable impurity in synthetic ethanol, in concentrations of 20 to 500 ppm. Example 15 discloses a qualitative reduction of peroxides in tetrahydrofuran, such reduction being monitored by qualitative analysis employing an iodide test in which an intense red-brown color will indicate the presence of substantial peroxide.

It has now been unexpectedly found that treatment with metal hydrides will convert hydroperoxides in allyl-alkyl ethers to acrolein and other decomposition products not harmful to the hydroformylation reaction, and will then reduce the acrolein to propanol and/or propionaldehyde without reducing the olefinic double bond in the allyl-alkyl ether. The novel metal hydride treatment will eliminate the catalyst induction period present in the hydroformylation reaction when partially oxidized allyl-alkyl ether is employed as a feedstock for conversion to its corresponding ether aldehyde. This is because the treatment will free the rhodium catalyst for the hydroformylation reaction, eliminating the competing acrolein to propanol and/or propionaldehyde reaction. See Table I below.

DESCRIPTION OF THE INVENTION

This invention is directed to a process for the selective reduction, by use of metal hydrides, of hydroperoxides in allyl-alkyl ethers to their decomposition products, including acrolein, and for the reduction of the acrolein produced to propanol and/or propionaldehyde, without reduction of the allyl-alkyl ethers. Thus, this invention is highly useful because acrolein is a rhodium catalyst inhibitor, and propanol and propionaldehyde are not inhibitors.

Allyl-alkyl ether, while being stored, will develop a hydroperoxide content as a result of the adventitious entry of air. These hydroperoxides can be decomposed to form acrolein and other impurities according to the following scheme:

$$CH_2=CH-CH_2-O-R + O_2 \longrightarrow$$

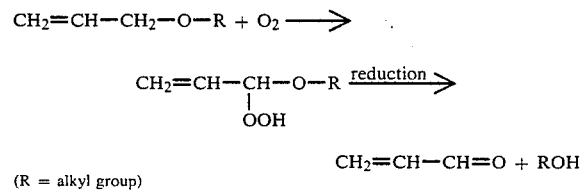

(R = alkyl group)

When an allyl-alkyl ether, such as allyl tert-butyl ether ("ATBE"), containing hydroperoxides is used as a hydroformylation reaction feedstock, a catalyst induction period is observed. It is believed that this induction period results from the competition for the rhodium catalyst* between the hydroformylation reaction ($k_1$ below) and the reduction of acrolein to propanol and propionaldehyde ($k_2$ below).

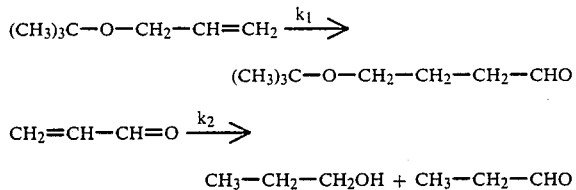

Thus, the metal hydride treatment eliminates the observed catalyst induction period because the $k_2$ reaction is eliminated by the prior reduction of acrolein, thereby allowing the rhodium catalyst to effect the $k_1$ reaction unfettered by the competing acrolein reduction reaction. This is supported by experimental data which shows the induction period is eliminated by the removal of hydroperoxides and acrolein from the ATBE. (See Examples 2-4 in Table I below).

*European patent application No. 18161 discloses that the preferred hydroformylation catalyst to create the aldehyde ether is a rhodium complex catalyst comprising rhodium in complex combination with carbon monoxide and a triorganophosphine ligand, such as triphenylphosphine. In addition, the reaction mixture typically includes up to about 100 moles or more of excess free triorganophosphine per gram atom of rhodium. When triphenylphosphine is employed as the ligand, this compound can destroy peroxides but will have no effect on acrolein when acrolein is at low concentrations.

Alumina appears unsatisfactory for the purification of large quantities of ATBE because acrolein is adsorbed rather than reduced. Thus, although experimentation has shown that hydroperoxide and acrolein free ATBE can be produced by passing the ether through an alumina column (see Example 2 in Table I below), such process is not commercially desirable because of the necessity of having to periodically wash the alumina bed free of the adsorbed acrolein and hydroperoxides. In a commercial operation which is operated continuously, one would have to employ multi-columns containing alumina and shift the liquid flow from one to another in order to avoid breakthrough of acrolein and/or hydroperoxide, and then regenerate the beds by washing them free of adsorbed and occluded acrolein and/or hydroperoxide while the beds are not in use.

It was found that treatment with a metal hydride decomposes the allyl-alkyl ether hydroperoxides to acrolein and alkyl alcohol and then further reduces the rhodium catalyst inhibitor acrolein to propionaldehyde and propanol, without reduction of the allyl-alkyl ether according to the following scheme:

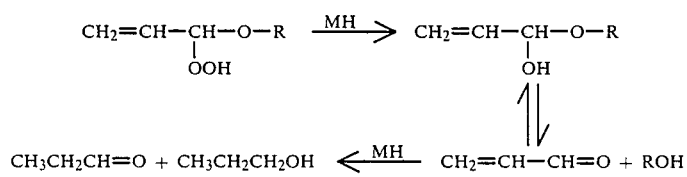

where MH is a metal hydride.

For this invention, the term metal hydride includes metal containing compounds which contain at least one hydrogen bonded to a metal or a non-metal and which can release the hydrogen by elevation of temperature or by addition of a decomposition agent, viz. acid. Representative metal hydrides include:

alkali metal (Na, Li, K, Cs, Rb) and alkaline earth metal (Ca, Mg, Be) borohydrides. ($MBH_4$)
trialkylborohydrides, including
  lithium triethyl borohydride [$Li(C_2H_5)_3BH$]
  lithium tributyl borohydride [$Li(C_4H_9)_3BH$]
  lithium triisobutylborohydride $Li[CH_2CH(CH_3)_2]_3BH$
lithium aluminum hydride ($LiAlH_4$)
lithium-tri-tert-butoxyaluminohydride [$Li(t\text{-}BuO)_3AlH$]
lithium-tri-ethoxyaluminohydride [$Li(EtO)_3AlH$]
sodium bis (2-methoxyethoxy) aluminum hydride [$Na(CH_3OCH_2CH_2O)_2AlH_2$, Vitride TM]

The allyl-alkyl ethers from which hydroperoxides and acrolein may be removed via the novel process are of the formula:

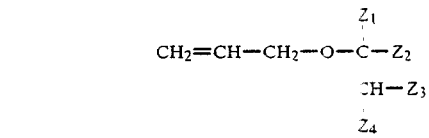

wherein $Z_1$ and $Z_2$, each independently of the other, represent a $C_1$ to $C_4$ alkyl radical, and $Z_3$ and $Z_4$ each, independently of the other, represent a hydrogen atom or a $C_1$ to $C_3$ alkyl radical, or wherein $Z_1$ represents a $C_1$ to $C_4$ alkyl radical, $Z_2$ and $Z_3$ together with the carbon atoms to which they are attached form a 5-membered or 6-membered cycloaliphatic ring, and $Z_4$ represents a hydrogen atom or a $C_1$ to $C_3$ alkyl radical. Representative allyl-alkyl ethers include:

allyl tert-butyl ether
allyl 2-methylbut-2-yl ether
allyl 2,3-dimethylbut-2-yl ether
allyl 3-methylpent-3-yl ether
allyl 3-ethylhex-3-yl ether
allyl 5-propylnon-5-yl-ether
allyl 1-methylcyclohexyl ether
allyl 1-methylcyclopentyl ether One preferred embodiment of this discovery involves the use of aqueous sodium borohydride to reduce hydroperoxides and to then reduce acrolein in allyl-alkyl ethers. When ATBE was treated with sodium borohydride, its hydroformylation reaction showed no catalyst inhibition (See Example 3 in Table 1).

Sodium borohydride is preferred to the other above metal hydrides as it is stable in basic water solutions. Moreover, solutions of sodium borohydride in polyethers are available commercially. The alkali trialkylborohydrides are also commercially available in solutions, but are more expensive than sodium borohydride. Lithium aluminum hydride and its derivatives, including Vitride TM are in one respect less favorable than sodium borohydride since they are very reactive with water and alcohols, thereby liberating hydrogen, which is potentially dangerous.

A 2-100 fold molar excess of metal hydride, based on moles of hydroperoxide, should be used to ensure the removal of hydroperoxide. Five to sixty minutes contact time of the borohydride solution with the allyl-alkyl ether is generally sufficient to effect the desired reduction though longer or shorter periods may be used. A borohydride should be used as a solution in a strong base, such as sodium hydroxide, to stabilize the aqueous borohydride as well as to stabilize the allyl-alkyl ether against hydrolysis to allyl alcohol. The concentration of sodium hydroxide can vary from 0.5N to 10N, with a preferred concentration being 1N. At the end of the reaction the ether should be washed with a sufficient amount of deoxygenated water to eliminate dissolved sodium hydroxide and borohydride. The borohydride treatment and particularly the water washings should be done under a nitrogen blanket to avoid air oxidation of the allyl-alkyl ether.

The reduction of hydroperoxide occurs rapidly at room temperature, but the reaction can be conducted at lower or higher temperatures (0° C. to 100° C.) if desired.

The concentration of sodium borohydride may vary within the range of its solubility at the particular temperature, e.g., at room temperature it can vary from 1 g to 55 g of sodium borohydride per 100 g of water.

The metal hydride can be provided in an insoluble form to allow facile separation in a liquid-solid system. This embodiment involves the use of resin immobilized borohydride counterions. According to U.S. Pat. No. 4,107,099, at column 1 lines 65 et seq., the anion exchange resins that are useful for the creation of immobilized borohydride counterions are those that are strongly basic, for example, the crosslinked quartenary ammonium polystyrene anion exchange resins of the gel or macroreticular types.

It was found that immobilized borohydride on Amberlyst TM A-26 anion exchange resin (prepared in accordance with U.S. Pat. No. 4,107,099 to Ventron) (see Example 4 below), was extremely effective in decomposing allyl-tert-butyl ether hydroperoxides and thus in eliminating the inhibitory effects of its decomposition product acrolein on the rhodium catalyst during ATBE hydroformylation. TM Rohm and Haas. When a hydroperoxide-contaminated stream of ATBE was passed through a packed glass column of borohydride-exchanged Amberlyst A-26, the hydroperoxides were destroyed quantitatively and the ATBE that eluted from the column showed no catalyst inhibition in its hydroformylation reaction. See results for Example 4 in Table I below.

For this batch-type embodiment of the invention, the amount of resin to be used is determined by the maximum loading capacity and the amount of peroxide in the ATBE feedstock. U.S. Pat. No. 4,107,099 discloses that the maximum loading capacity is about 3.7–3.8 meq. of boron per gram dry resin for gel type resins (e.g., Amberlite TM IRA-900) whereas loading capacity is 4.1–4.2 meq. of boron per gram of dry resins for macroreticular type resins (e.g., Amberlyst TM A-26). The treatment with the borohydride resin can be done at about room temperature, viz. 23° C., although higher (viz. up to 75° C.) or lower temperatures (viz. down to 0° C.) are also suitable so long as the effectiveness of the treatment is achieved.

A third preferred embodiment of this invention involves the implementation of the immobilized borohydride resins into a system which permits a continuous flow of allyl-alkyl ether, free of hydroperoxides and aldehydes, into a hydroformylation reactor. In this system, a series of guard beds of borohydride resins are included in the process scheme to ensure that the hydroperoxides and aldehydes are removed from the feedstock prior to such feedstock's entry into a hydroformylation reactor. This will protect catalyst activity while avoiding a separate treatment of the feedstock. The final bed in such system consists of an adsorbent, such as another anion exchange resin bed or silica gel, which possesses the ability to trap any boric acid, boride salt or entrained borohydrides in the allyl-alkyl ether effluent and thus avoid any contamination of the main hydroformylation catalyst solution.

As in the second embodiment, above, the amount of resin necessary for this continuous feed system is to be based upon the maximum loading capacity of the resin as well as the amount of hydroperoxide in the allyl-alkyl ether feedstock. Room temperature, about 23° C., is preferable although higher or lower temperatures are also suitable.

Other systems for purification are also possible. Thus, an effective process would comprise (a) treating the allyl-alkyl ether with metal hydride in alkaline aqueous solution; (b) passing the ether effluent through a borohydride resin bed; and (c) washing the ether with sufficient deoxygenated water to eliminate dissolved metal hydride and alkali (e.g., sodium hydroxide).

EXAMPLES

The following general procedure was followed in determining the hydroformylation reaction rate in all the examples below:

Hydroformylation rates were determined in a 100-ml stainless steel autoclave equipped with magnetic stirring. The autoclave was heated by a 200-watt band heater equipped with a proportional temperature controller. Internal temperature was monitored with a platinum resistance thermometer of ±0.1° accuracy.

The autoclave was connected to a gas manifold for initial pressurization with reactant gases. An external reservoir of 0.5 liter capacity containing $CO:H_2$ in 1:1 molar proportion was connected to the autoclave by means of a Research Control TM motor valve. In order to measure pressure in the reaction chamber the autoclave was also equipped with a 100–135 psi pressure transmitter. During hydroformylation the autoclave was maintained at 120 psig via the external reservoir/motor valve/pressure transmitter. Reaction rate was calculated from the rate of pressure drop in the external reservoir.

EXAMPLE 1

Control-ATBE containing 0.17 percent peroxide.

20 ml of catalyst solution, containing 200 ppm rhodium as $RhH(CO)(Ph_3P)_3$ and 10% triphenylphosphine, in n-butyraldehyde trimer solvent, was charged to a preheated reactor at 70° C. After the temperature of the catalyst solution equilibrated to 70° C. 5.7 grams of ATBE containing 0.17 weight % hydroperoxide was injected into the reactor followed by 40 p.s.i. $H_2$, 20 p.s.i. CO and nitrogen to a total of 120 p.s.i. The autoclave was then opened to the motor valve-reservoir assembly. The hydroformylation reaction uses CO and $H_2$ in 1:1 molar proportions. Carbon monoxide and hydrogen were fed in at 1:1 ($CO:H_2$) molar proportions to keep the pressure constant. The reaction rates obtained for the hydroformylation of ATBE to 4-tertbutoxybutyraldehyde are summarized in Table I below, under Example 1.

EXAMPLE 2

ATBE purified with activated alumina.

A 50 cm×2 cm glass chromatographic column was packed with 50 g. activated alumina (ICN Pharmaceuticals, activity Grade I). A 200-ml commercial ATBE sample containing 0.17 weight % of hydroperoxide was passed through the column at a rate of 1.6 ml/min. A total of 180 ml ATBE was eluted from the column and recovered, the other 20 ml being retained by the column. The eluted ATBE gave no inhibition in its hydroformylation reaction, when hydroformylated in accordance with the procedure of Example 1 above. Hydroformylation rates were determined as described above. The results are summarized under Example 2 in Table 1.

The qualitative analysis of the eluted ATBE and the alumina indicated that the hydroperoxides and acrolein had merely been adsorbed rather than reduced. The following procedure was employed to conduct such qualitative analysis:

Silica gel coated strips (10×3 cm) (Supplier: Eastman Kodak) were used as thin layer chromatography ("tlc") plates. A spot of ATBE (or a solution of it in CHCl₃) was applied on the tlc plate and the plate was developed with chloroform. After the development plate had dried, the visualization reagent* was sprayed on. In a few minutes a pink spot with Rf=0.4, i.e., the ratio of the distance moved by the hydroperoxide to the distance moved by the chloroform, developed corresponding to ATBE hydroperoxide. The intensity of the spot corresponds to the amount of hydroperoxide present.
*To make the visualization reagent, 1.5 g N,N-dimethyl-para-phenylenediamine was dissolved in 20 ml water containing 1 ml acetic acid. The solution was then diluted with methanol to 100 ml, flushed with nitrogen and stored in the refrigerator.

Using the above method it was found that the ATBE eluted from the alumina column contained no hydroperoxides.

The alumina column was then washed with a total of 75 ml of methanol which was collected in three separate 25-ml portions. Qualitative analysis employing gas chromatography showed that the middle 25-ml portion of the methanol collected contained acrolein.

EXAMPLE 3

ATBE purified with Aqueous NaBH₄.

To a 100-ml three-neck flask equipped with mechanical stirrer, reflux condenser and nitrogen inlet, were added 15 ml partially oxidized ATBE and 10 ml of 10% solution of sodium borohydride in 1N sodium hydroxide. The mixture was stirred at 23° C. for 1 hour, and then transferred to a separatory funnel under nitrogen. The organic layer was separated and washed three times with five-ml portions of degassed water. The ATBE purified in this fashion showed no catalyst inhibition in its hydroformylation reaction rate, when hydroformylated in accordance with the procedure of Example 1 above. See the results for Example 3 in Table I.

EXAMPLE 4

ATBE purified by borohydride exchange resin.

The method described in U.S. Pat. No. 4,107,099 (Example 1) was followed. Amberlyst A-26, strong base chloride form anion exchange resin (150 g), was slurry packed with water in a 50×3 cm glass column. The resin was washed successively with 2 liters of water, 1 liter ethanol and 1 liter of water. 1.8 liters of solution of sodium borohydride in sodium hydroxide (1 weight % NaBH₄ in 2.6 weight % NaOH solution) was passed through the resin over a period of 1.5 hours. The resin was then washed with 1 liter water followed by 200 ml ethanol.

A 200 ml sample of partially oxidized ATBE (0.3 weight % hydroperoxide) was passed through the column at a rate of 3 ml/min. The column effluents showed no catalyst inhibition in a hydroformylation reaction proving that acrolein was also destroyed in this treatment. See the results for Example 4 in Table I.

TABLE 1

| Example 1 ATBE containing 0.17% peroxide | | Example 2 ATBE purified with activated alumina | | Example 3 ATBE purified with aqueous alkali sodium borohydride | | Example 4 ATBE purified with borohydride exchange resin | |
|---|---|---|---|---|---|---|---|
| Time^a | Rate^b | Time | Rate | Time | Rate | Time | Rate |
| 3.7 | 0 | 3.1 | 1.68 | 2.3 | 2.21 | 4.0 | .18 |
| 9.5 | 0.86 | 7.6 | 1.61 | 5.6 | 1.67 | 8.0 | .18 |
| 13.5 | 1.36 | 10.9 | 1.79 | 10.6 | 1.83 | 11.8 | .23 |
| 17.5 | 1.45 | | | 16.2 | 1.89 | | |
| 21.1 | 1.47 | | | | | | |

^a time in minutes
^b reaction rate in g moles/L hr.

What is claimed is:

1. In a rhodium catalyzed hydroformylation process for producing an ether aldehyde by reacting an allyl-alkyl ether feedstock with carbon monoxide and hydrogen, said allyl-alkyl ether being selected from the group consisting of allyl tert-butyl ether, allyl 2,3-dimethylbut-2-yl ether, allyl 2-methylbut-2-yl ether, allyl 3-methylpent-3-yl ether, allyl 3-ethylhex-3-yl ether, allyl 5-propylnon-5-yl ether, allyl 1-methylcyclohexyl ether, and allyl 1-methylcyclopentyl ether, the improvement which comprises employing as the allyl-alkyl feedstock, an allyl-alkyl ether feedstock which has been treated with sodium borohydride in alkaline aqueous solution to form an organic containing layer which is separated under an inert gas blanket and washed with degassed water, so as to convert hydrogen peroxide present in said allyl-alkyl ether feedstock to decomposition products, including $\alpha,\beta$-unsaturated aldehydes, and reduce such $\alpha,\beta$-unsaturated aldehydes to alcohols.

2. In a rhodium catalyzed hydroformylation process for producing an ether aldehyde by reacting an allyl-alkyl ether feedstock with carbon monoxide and hydrogen, said allyl-alkyl ether being selected from the group consisting of allyl tert-butyl ether, allyl 2,3-dimethylbut-2-yl ether, allyl 2-methylbut-2-yl ether, allyl 3-methylpent-3-yl ether, allyl 3-ethylhex-3-yl ether, allyl 5-propylnon-5-yl ether, allyl 1-methylcyclohexyl ether, and allyl 1-methylcyclopentyl ether, the improvement which comprises employing as the allyl-alkyl ether feedstock, an allyl-alkyl ether feedstock which has been treated by passing the allyl-alkyl ether feedstock through an anion exchange resin containing immobilized borohydride counterions thereon, so as to convert hydrogen peroxide present in said allyl-alkyl ether feedstock to decomposition products, including $\alpha,\beta$-unsaturated aldehydes, and reduce such $\alpha,\beta$-unsaturated aldehydes to alcohols.

3. In a rhodium catalyzed hydroformylation process for producing an ether aldehyde by reacting an allyl-alkyl ether feedstock with carbon monoxide and hydrogen, said allyl-alkyl ether being selected from the group consisting of allyl tert-butyl ether, allyl 2,3-dimethylbut-2-yl ether, allyl 2-methylbut-2-yl ether, allyl 3-methylpent-3-yl ether, allyl 3-ethylhex-3-yl ether, allyl 5-propylnon-5-yl ether, allyl 1-methylcyclohexyl ether, and allyl 1-methylcyclopentyl ether, the improvement which comprises employing as the allyl-alkyl ether feedstock, an allyl-alkyl ether feedstock which has been treated with sodium borohydride in alkaline aqueous solution to obtain an ether effluent which is passed through a bed of anion exchange resin containing immobilized borohydride counterions and the ether effluent washed with sufficient deoxygenated water to eliminate dissolved alkali and an alkaline aqueous solution to metal hydride, so as to convert hydrogen peroxide present in said allyl-alkyl ether feedstock to decomposition products, including $\alpha,\beta$-unsaturated aldehydes, and reduce such $\alpha,\beta$-unsaturated aldehydes to alcohols.

4. The process of claim 2 wherein the allyl-alkyl ether feedstock is passed through a series of beds, the first several beds containing such anion exchange resins and the last bed comprising an absorbent capable of retaining entrained borohydride, boric acid, or boride salt present in the ether effluent.

* * * * *